(12) United States Patent
Speakman

(10) Patent No.: US 6,492,293 B1
(45) Date of Patent: Dec. 10, 2002

(54) POLYMERISATION CATALYST

(75) Inventor: John Gabriel Speakman, Martigues (FR)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/702,770

(22) Filed: Nov. 1, 2000

(30) Foreign Application Priority Data

| Nov. 12, 1999 | (EP) | ............................................ 99430028 |
| Nov. 12, 1999 | (EP) | ............................................ 99430029 |
| Jan. 21, 2000 | (GB) | ............................................ 0001467 |
| Jan. 21, 2000 | (GB) | ............................................ 0001468 |

(51) Int. Cl.⁷ ........................ B01J 31/00; B01J 37/00; C08F 4/02; C08F 4/60

(52) U.S. Cl. ...................... 502/129; 502/132; 502/167; 502/107

(58) Field of Search ................ 502/107, 129, 502/132, 167

(56) References Cited

U.S. PATENT DOCUMENTS

| 3,668,146 A | * | 6/1972 | Ruhle | .......................... 252/428 |
| 4,119,773 A | | 10/1978 | Speca | .......................... 526/130 |
| 4,188,471 A | | 2/1980 | Nasser, Jr. et al. | ........... 526/96 |
| 4,189,402 A | | 2/1980 | Rekers et al. | ................ 252/428 |
| 4,295,999 A | | 10/1981 | Slaugh | ........................ 252/455 |
| 6,117,959 A | * | 9/2000 | Ponaski, Jr. et al. | ........ 502/162 |

FOREIGN PATENT DOCUMENTS

| DE | 198 06 435 A1 | | 8/1999 |
| GB | 1 314 005 | | 4/1973 |
| WO | WO 96/23010 | * | 8/1996 |
| WO | WO 97/48735 | * | 12/1997 |
| WO | WO99/12981 | | 3/1999 |
| WO | WO 99/12981 | * | 3/1999 |
| WO | WO 99/46304 | * | 9/1999 |
| WO | WO 00/22011 | | 4/2000 |

OTHER PUBLICATIONS

Elisabeta Alexiu et al., "Catalyst for the polymerization of olefins," *Chemical Abstracts*, vol. 103, No. 10, Sep. 9, 1985.

* cited by examiner

*Primary Examiner*—Mark L. Bell
*Assistant Examiner*—J. Pasterczyk
(74) *Attorney, Agent, or Firm*—Finnegan, Henderson, Farabow, Garrett and Dunner, L.L.P.

(57) ABSTRACT

A catalyst for the polymerisation and copolymerisation of 1-olefins is disclosed which comprises 1) a late transition metal complex
2) optionally an activating quantity of an activator compound, and
3) a support which has been impregnated with titanium or aluminium, and calcined at a temperature of between 200° C. and 1000° C., said calcining being after impregnation in the case of aluminium.

44 Claims, No Drawings

POLYMERISATION CATALYST

The present invention relates to a novel catalysts for the polymerisation and copolymerisation of 1-olefins.

The use of certain transition metal compounds to polymerise 1-olefins, for example, ethylene or propylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer.

Our own WO99/12981 discloses that 1-olefins may be polymerised by contacting it with certain transition metal, particularly iron, complexes of selected 2,6-pyridinecarboxaldehydebis(imines) and 2,6-diacylpyridinebis(imines). Catalyst supports such as silica, alumina and zirconia are disclosed.

We have discovered that when late transition metal complexes are supported on silica impregnated with titanium or aluminium, improvements in both the polymerisation process and the polymer product may be obtained.

Accordingly, the present invention provides a catalyst for the polymerisation and copolymerisation of 1-olefins, comprising
1) a late transition metal complex,
2) optionally an activating quantity of an activator compound, and
3) a support which has been impregnated with titanium or aluminium, and calcined at a temperature of between 200° C. and 1000° C., said calcining being after impregnation in the case of aluminium.

By "late transition metal" is meant a metal from Groups VIIIb or Ib (Groups 8–11) of the Periodic Table. In particular the metals Fe, Co, Ni, Ru, Rh, Pd, Os, Ir, and Pt are preferred, especially Fe, Co and Ni.

Preferably the support comprises silica, alumina, zirconia, talc, kieselguhr or magnesia.

Preferably the activator is selected from organoaluminium compounds and hydrocarbylboron compounds.

It is preferred that the titanium incorporated into the support is selected from compounds represented by the formulae (a) $(R')_n Ti(OR')_m$; (b) $(RO)_m Ti(OR')_n$; (c) $TiX_4$; (d) $TiO_2$; (e) titanium acetylacetone compounds and (f) alkanolamine titanates wherein m is 1,2,3 or 4; n is 0,1,2 or 3; m+n=4; the R group is selected from alkyl, aryl, cycloalkyl, and combinations thereof, for example arylalkyl and alkaryl, each group R having 1 to 12 carbon atoms; R' is selected from the group consisting of R, cyclopentadienyl and alkenyl, for example ethenyl, propenyl, and isopropenyl each group R' having 1 to 12 carbon atoms; X is halogen, preferably chlorine when more than one R (or R') group occurs in the titanium compound the groups can be the same or different. The titanium acetylacetonate compound can be, for example, titanium triacetylacetonate, titanium dichlorodiacetylacetonate or titanium dichlorodi(isopropoxide). Titanium compounds represented by the formula $(RO)_4 Ti$ are preferred, particularly the alkyl compounds having from 1 to 6 carbon atoms in each alkyl group for example, titanium tetramethoxide, titanium tetraethoxide, titanium tetraisopropoxide, titanium tetrabutoxide.

It is preferred that the aluminium impregnated into the support silica is selected from compounds represented by the formulae (a) $(R')_n Al(OR')_m$; (b) $(RO)_m Al(OR')_n$; (c) $(R')_n Al(X)_m$; (d) $Al_2O_3$; (e) aluminium acetylacetonate compounds and (f) alkanolamine aluminates wherein m is 0,1,2 or 3; n is 0,1,2 or 3; m+n=3; the R group is selected from alkyl, aryl, cycloalkyl, and combinations thereof, for example arylalkyl and alkaryl, each group R having 1 to 12 carbon atoms; R' is selected from the group consisting of R, cyclopentadienyl and alkenyl, for example ethenyl, propenyl, and isopropenyl each group R' having 1 to 12 carbon atoms; X is halogen preferably chlorine; when more than one R (or R') group occurs in the aluminium compound the groups can be the same or different. The aluminium acetylacetonate compound can be, for example, aluminium acetylacetonate diisopropoxide, aluminium dichloro acetylacetonate. The alkanolarine aluminate can be for example triethanolamine aluminate. Aluminium compounds represented by the formula $R_3Al$ are preferred, particularly the alkyl compounds having from 1 to 6 carbon atoms in each alkyl group for example trimethyl aluminium, triethyl aluminium and tri-isobutyl aluminium.

A further aspect of the present invention is a process for the preparation of a supported catalyst, comprising the steps of:
preparing a support, including the steps of adding to the fluidised support a titanium or aluminium compound, preferably as defined above, and then calcining the resulting titanium- or aluminium-treated support at a temperature of between 200 and 1000° C.;
and then adding to the support a late transition metal complex and optionally an activating quantity of an activator compound.

The invention also comprises in another aspect the use of titanium or aluminium impregnation to improve the activity of a late transition metal olefin polymerisation catalyst.

The invention also comprises in another aspect the use of titanium or aluminium impregnation to alter the melt index ratio or molecular weight distribution in a polymer formed using as catalyst a late transition metal olefin complex.

Preferably the amount of titanium incorporated in the support is from 0.1 to 5 wt %, more preferably from 3 to 4.5 wt %. Preferably the amount of aluminium impregnated in the silica is from 0.1 to 10 wt %, more preferably from 1 to 6 wt %, and most preferably from 1.5 to 2.5 wt %.

Generally the calcining temperature is most conveniently between 200° C. and the sintering temperature of the support; preferably between 300 and 850° C., and more preferably between 400 and 750° C. It is preferred that this calcination takes place under a flow of a dry gas containing a minimum of 1% (v/v) of oxygen. Dry air is often used.

Preferably the support is additionally calcined at a temperature of between 250° C. and the sintering temperature of the support before the titanium or aluminium is impregnated into the support (as well as after this impregnation).

If desired the supported catalysts of the invention can be formed in situ in the presence of the support material, or the support material (having been treated with the titanium or aluminium compound) can be pre-impregnated or premixed, simultaneously or sequentially, with one or more of the catalyst components. For example, formation of the supported catalyst can be achieved by treating the complex of Formula (I) with the activator (2) (when present) in a suitable inert diluent, for example a volatile hydrocarbon, slurrying the titanium-impregnated support with the product and evaporating the volatile diluent. The produced supported catalyst is preferably in the form of a free-flowing powder. The quantity of support employed can vary widely, for example from 100,000 to 1 grams per gram of late transition metal metal present.

The late transition metal complex may comprise bidentate or tridentate ligands, preferably coordinated to the metal through nitrogen atoms. As examples are those complexes disclosed in WO 96/23010.

Preferably the late transition metal complex comprises a complex of the formula

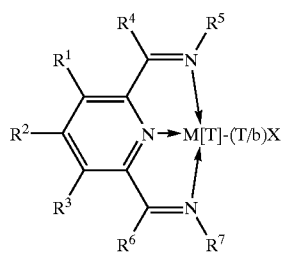

Formula (I)

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^7$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl, substituted heterohydrocarbyl.

In the complex of Formula (I), $R^5$ and $R^7$ are preferably independently selected from substituted or unsubstituted alicyclic, heterocyclic or aromatic groups, for example, phenyl, 1-naphthyl, 2-naphthyl, 2-methylphenyl, 2-ethylphenyl, 2,6-diisopropylphenyl, 2,3-diisopropylphenyl, 2,4-diisopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro2,6-diethylphenyl, and 2,6,bis (2,6-dimethylphenyl)phenyl, cyclohexyl and pyridinyl.

In a preferred embodiment $R^5$ is represented by the group "P" and $R^7$ is represented by the group "Q" as follows:

Group P

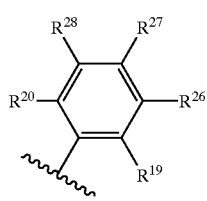

-continued

Group Q

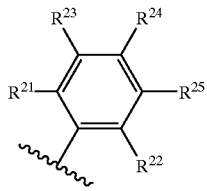

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents.

The ring systems P and Q are preferably independently 2,6-hydrocarbylphenyl or fused-ring polyaromatic, for example, 1-naphthyl, 2-naphthyl, 1-phenanthrenyl and 8-quinolinyl.

Preferably at least one of $R^{19}$, $R^{20}$, $R^{21}$ and $R^{22}$ is hydrocarbyl, substituted hydrocarbyl, heterohydrocarbyl or substituted heterohydrocarbyl. More preferably at least one of $R^{19}$ and $R^{20}$, and at least one of $R^{21}$ and $R^{22}$, is hydrocarbyl, substituted hydrocarbyl, heterohydrocarbyl or substituted heterohydrocarbyl. Most preferably $R^{19}$, $R^{20}$, $R^{21}$ and $R^{22}$ are all independently selected from hydrocarbyl, substituted hydrocarbyl, heterohydrocarbyl or substituted heterohydrocarbyl. $R^{19}$, $R^{20}$, $R^{21}$ and $R^{22}$ are preferably independently selected from methyl, ethyl, n-propyl, iso-propyl, n-butyl, sec-butyl, tert.-butyl, n-pentyl, neopentyl, n-hexyl, 4-methylpentyl, n-octyl, phenyl and benzyl.

$R^1$, $R^2$, $R^3$, $R^4$, $R^6$, $R^{19}$, $R^{20}$, $R^{21}$, $R^{22}$, $R^{23}$, $R^{25}$, $R^{26}$ and $R^{28}$ are preferably independently selected from hydrogen and $C_1$ to $C_8$ hydrocarbyl, for example, methyl, ethyl, n-propyl, n-butyl, t-butyl, n-hexyl, n-octyl, phenyl and benzyl.

In an alternative embodiment $R^5$ is a group having the formula $-NR^{29}R^{30}$ and $R^7$ is a group having the formula $-NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents.

Each of the nitrogen atoms is coordinated to the metal by a "dative" bond, ie a bond formed by donation of a lone pair of electrons from the nitrogen atom. The remaining bonds on each of these atoms are covalent bonds formed by electron sharing between the atoms and the organic ligand as shown in the defined formula for the metal complex illustrated above.

The atom or group represented by X in the compounds of Formula (I) can be, for example, selected from halide, sulphate, nitrate, thiolate, thiocarboxylate, $BF_4^-$, $PF_6^-$, hydride, hydrocarbyloxide, carboxylate, hydrocarbyl, substituted hydrocarbyl and heterohydrocarbyl, or β-diketonates. Examples of such atoms or groups are chloride, bromide, methyl, ethyl, propyl, butyl, octyl, decyl, phenyl, benzyl, methoxide, ethoxide, isopropoxide, tosylate, triflate, formate, acetate, phenoxide and benzoate. Preferred examples of the atom or group X in the compounds of Formula (I) are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

The following are examples of nitrogen-containing transition metal complexes that can be employed in the catalyst of the present invention:

2,6-diacetylpyridinebis(2,6-diisopropylanil)FeCl$_2$
2,6-diacetylpyridinebis(2,6-diisopropylanil)MnCl$_2$
2,6-diacetylpyridinebis(2,6-diisopropylanil)CoCl$_2$
2,6-diacetylpyridinebis(2-tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl$_2$
2,6-diacetylpyridinebis(2,4,6 trimethyl anil)FeCl$_2$
2,6-diacetylpyridinebis(2,6-dimethyl 4-t-butyl anil)FeCl$_2$
2,6-dialdiminepyridinebis(2,6-dimethylanil)FeCl$_2$
2,6-dialdiminepyridinebis(2,6-diethylanil)FeCl$_2$
2,6-dialdiminepyridinebis(2,6-diisopropylanil)FeCl2
2,6-dialdiminepyridinebis(1-naphthil)FeCl$_2$ and
2,6-bis(1,1-diphenylhydrazone)pyridine.FeCl$_2$.

The catalysts of the present invention can if desired comprise more than one of the above-mentioned compounds. The catalysts can also include one or more other types of catalyst, such as those of the type used in conventional Ziegler-Natta catalyst systems, metallocene-based catalysts, monocyclopentadienyl- or constrained geometry based catalysts, or heat activated supported chromium oxide catalysts (e.g. Phillips-type catalyst). The optional activator (2) in the catalysts of the invention is preferably selected from organoaluminium compounds and hydrocarbylboron compounds. Suitable organoaluminium compounds include compounds of the formula AlR$_3$, where each R is independently C$_1$–C$_{12}$ alkyl or halo. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof Commercially available alumoxanes are generally believed to be mixtures of linear and cyclic compounds. The cyclic alumoxanes can be represented by the formula [R$^{16}$AlO]$_s$ and the linear alumoxanes by the formula R$^{17}$(R$^{18}$AlO)$_s$ wherein s is a number from about 2 to 50, and wherein R$^{16}$, R$^{17}$, and R$_{18}$ represent hydrocarbyl groups, preferably C$_1$ to C$_6$ alkyl groups, for example methyl, ethyl or butyl groups. Alkylalumoxanes such as methylalumoxane (MAO) are preferred.

Mixtures of alkylalumoxanes and trialkylaluminium compounds are particularly preferred, such as MAO with TMA or TIBA. In this context it should be noted that the term "alkylalumoxane" as used in this specification includes alkylalumoxanes available commercially which may contain a proportion, typically about 10 wt %, but optionally up to 50 wt %, of the corresponding trialkylaluminium; for instance, commercial MAO usually contains approximately 10 wt % trimethylaluminium (TMA), whilst commercial MMAO contains both TMA and TIBA. Quantities of alkylalumoxane quoted herein include such trialkylaluminium impurities, and accordingly quantities of trialkylaluminium compounds quoted herein are considered to comprise compounds of the formula AlR3 additional to any AlR$_3$ compound incorporated within the alkylalumoxane when present.

Examples of suitable hydrocarbylboron compounds are boroxines, trimethylboron, triethylboron, dimethylphenylammoniumtetra(phenyl)borate, trityltetra (phenyl)borate, triphenylboron, dimethylphenylammonium tetra(pentafluorophenyl)borate, sodium tetrakis[(bis-3,5-trifluoromethyl)phenyl]borate, H$^+$(OEt$_2$)[(bis-3,5-trifluoromethyl)phenyl]borate, trityltetra (pentafluorophenyl)borate and tris(pentafluorophenyl) boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per atom of late transition metal.

An alternative class of activators comprise salts of a cationic oxidising agent and a non-coordinating compatible anion. Examples of cationic oxidising agents include: ferrocenium, hydrocarbyl-substituted ferrocenium, Ag$^+$, or Pb$^{2+}$. Examples of non-coordinating compatible anions are BF$_4^-$, SbCl$_6^-$, PF$_6^-$, tetrakis(phenyl)borate and tetrakis (pentafluorophenyl)borate.

The catalyst may also comprise a neutral Lewis base. Neutral Lewis bases are well known in the art of Ziegler-Natta catalyst polymerisation technology. Examples of classes of neutral Lewis bases suitable for the present invention are unsaturated hydrocarbons, for example, alkenes (other than 1-olefins) or alkynes, primary, secondary and tertiary amines, amides, phosphoramides, phosphines, phosphites, ethers, thioethers, nitriles, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention.

A preferred support is silica, and a preferred activator is methylalumoxane (MAO).

The present invention further provides a process for the polymerisation and copolymerisation of 1-olefins, comprising contacting the monomeric olefin under polymerisation conditions with the polymerisation catalyst of the present invention. A preferred process comprises the steps of:

a) preparing a prepolymer-based catalyst by contacting one or more 1-olefins with a catalyst, and b) contacting the prepolymer-based catalyst with one or more 1-olefins, wherein the catalyst is as defined above.

In the text hereinbelow, the term "catalyst" is intended to include "prepolymer-based catalyst" as defined above.

The polymerisation conditions can be, for example, solution phase, slurry phase, gas phase or bulk phase, with polymerisation temperatures ranging from −100° C. to +300° C., and at pressures of atmospheric and above, particularly from 140 to 4100 kPa. If desired, the catalyst can be used to polymerise ethylene under high pressure/high temperature process conditions wherein the polymeric material forms as a melt in supercritical ethylene. Preferably the polymerisation is conducted under gas phase fluidised bed or stirred bed conditions.

Suitable monomers for use in the polymerisation process of the present invention are, for example, ethylene and $C_{2-20}$ α-olefins, specifically propylene, 1-butene, 1-pentene, 1-hexene, 4-methylpentene-1, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene. Other monomers include methyl methacrylate, methyl acrylate, butyl acrylate, acrylonitrile, vinyl acetate, and styrene. Preferred monomers for homopolymerisation processes are ethylene and propylene.

The catalysts and process of the invention can also be used for copolymerising ethylene or propylene with each other or with other 1-olefins such as 1-butene, 1-hexene, 4-methylpentene-1, and octene, or with other monomeric materials, for example, methyl methacrylate, methyl acrylate, butyl acrylate, acrylonitrile, vinyl acetate, and styrene.

Irrespective of the polymerisation or copolymerisation technique employed, polymerisation or copolymerisation is typically carried out under conditions that substantially exclude oxygen, water, and other materials that act as catalyst poisons. Also, polymerisation or copolymerisation can be carried out in the presence of additives to control polymer or copolymer molecular weights.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase, bulk phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of complex employed in the catalyst system). This means that relatively very small quantities of late transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (e.g. as occurs in most commercial slurry and gas phase polymerisation processes), the amount of late transition metal complex in the produced polymer can be very small.

Slurry phase polymerisation conditions or gas phase polymerisation conditions are particularly useful for the production of high or low density grades of polyethylene, and polypropylene. In these processes the polymerisation conditions can be batch, continuous or semi-continuous. Furthermore, one or more reactors may be used, e.g. from two to five reactors in series. Different reaction conditions, such as different temperatures or hydrogen concentrations may be employed in the different reactors. In the slurry phase process and the gas phase process, the catalyst is generally metered and transferred into the polymerisation zone in the form of a particulate solid either as a dry powder (e.g. with an inert gas) or as a slurry. This solid can be, for example, a solid catalyst system formed from the one or more of complexes of the invention and an activator with or without other types of catalysts, or can be the solid catalyst alone with or without other types of catalysts. In the latter situation, the activator can be fed to the polymerisation zone, for example as a solution, separately from or together with the solid catalyst. Preferably the catalyst system or the transition metal complex component of the catalyst system employed in the slurry polymerisation and gas phase polymerisation is supported on one or more support materials. Most preferably the catalyst system is supported on the support material prior to its introduction into the polymerisation zone. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques. Once the polymer product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to the polymerisation zone.

In the slurry phase polymerisation process the solid particles of catalyst, or supported catalyst, are fed to a polymerisation zone either as dry powder or as a slurry in the polymerisation diluent. The polymerisation diluent is compatible with the polymer(s) and catalyst(s), and may be an alkane such as hexane, heptane, isobutane, or a mixture of hydrocarbons or paraffins. Preferably the particles are fed to a polymerisation zone as a suspension in the polymerisation diluent. The polymerisation zone can be, for example, an autoclave or similar reaction vessel, or a continuous loop reactor, e.g. of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

In bulk polymerisation processes, liquid monomer such as propylene is used as the polymerisation medium.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid in the polymerisation zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

For typical production of impact copolymers, homopolymer formed from the first monomer in a first reactor is reacted with the second monomer in a second reactor. For manufacture of propylene/ethylene impact copolymer in a gas-phase process, propylene is polymerized in a first reactor; reactive polymer transferred to a second reactor in which ethylene or other comonomer is added. The result is an intimate mixture of a isotactic polypropylene chains with chains of a random propylene/ethylene copolymer. A random copolymer typically is produced in a single reactor in which a minor amount of a comonomer (typically ethylene) is added to polymerizing chains of propylene.

Methods for operating gas phase fluidised bed processes for making polyethylene, ethylene copolymers and polypropylene are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and then returned to the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

Although not usually required, upon completion of polymerisation or copolymerisation, or when it is desired to terminate polymerisation or copolymerisation or at least temporarily deactivate the catalyst or catalyst component of this invention, the catalyst can be contacted with water, alcohols, acetone, or other suitable catalyst rdeactivators a manner known to persons of skill in the art.

Homopolymerisation of ethylene with the catalysts of the invention may produce so-called "high density" grades of polyethylene. These polymers have relatively high stiffness and are useful for making articles where inherent rigidity is required. Copolymerisation of ethylene with higher 1-olefins (e.g. butene, hexene or octene) can provide a wide variety of copolymers differing in density and in other important physical properties. Particularly important copolymers made by copolymerising ethylene with higher 1-olefins with the catalysts of the invention are the copolymers having a density in the range of 0.91 to 0.93. These copolymers which are generally referred to in the art as linear low density polyethylene, are in many respects similar to the so called low density polyethylene produced by the high pressure free radical catalysed polymerisation of ethylene. Such polymers and copolymers are used extensively in the manufacture of flexible blown film.

Propylene polymers produced by the process of the invention include propylene homopolymer and copolymers of propylene with less than 50 mole % ethylene or other alpha-olefin such as butene-1, pentene- 1,4-methylpentene-1, or hexene- 1, or mixtures thereof Propylene polymers also may include copolymers of propylene with minor amounts of a copolymerizable monomer. Typically, most useful are normally-solid polymers of propylene containing polypropylene crystallinity, random copolymers of propylene with up to about 10 wt. % ethylene, and impact copolymers containing up to about 20 wt. % ethylene or other alpha-olefin. Polypropylene homopolymers may contain a small amount (typically below 2 wt. %) of other monomers to the extent the properties of the homopolymer are not affected significantly.

Propylene polymers may be produced which are normally solid, predominantly isotactic, poly α-olefins. Levels of stereorandom by-products are sufficiently low so that useful products can be obtained without separation thereof Typically, useful propylene homopolymers show polypropylene crystallinity and have isotactic indices above 90 and many times above 95. Copolymers typically will have lower isotactic indices, typically above 80–85.

Depending upon polymerisation conditions known in the art, propylene polymers with melt flow rates from below 1 to above 1000 may be produced in a reactor. For many applications, polypropylenes with a MFR from 2 to 100 are typical. Some uses such as for spunbonding may use a polymer with an MFR of 500 to 2000.

Depending upon the use of the polymer product, minor amounts of additives are typically incorporated into the polymer formulation such as acid scavengers, antioxidants, stabilizers, and the like. Generally, these additives are incorporated at levels of about 25 to 2000 ppm, typically from about 50 to about 1000 ppm, and more typically 400 to 1000 ppm, based on the polymer.

In use, polymers or copolymers made according to the invention in the form of a powder are conventionally compounded into pellets. Examples of uses for polymer compositions made according to the invention include use to form fibres, extruded films, tapes, spunbonded webs, moulded or thermoformed products, and the like. The polymers may be blown into films, or may be used for making a variety of moulded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofutranone stabilizers, and the like. Various olefin polymer additives are described in U.S. Pat. Nos. 4,318,845, 4,325,863, 4,590,231, 4,668,721, 4,876,300, 5,175,312, 5,276,076, 5,326,802, 5,344,860, 5,596,033, and 5,625,090.

Fillers such as silica, glass fibers, talc, and the like, nucleating agents, and colourants also may be added to the polymer compositions as known by the art.

EXAMPLES

Example 1

Preparation of the Iron Complex as Catalyst Precursor 4 g of 2,6-diacetylpyridine, 10.32 ml of 2,4,6-trimethylaniline and 0.2 g of p-toluenesulphonic acid monohydrate were added to 150 ml of dry toluene in a 250 ml round bottomed flask. A 20 ml Dean-Stark heavy fractionating column and condenser were attached and the mixture heated with stirring to 160° C. The reaction appeared to have gone to completion in about 3 hours. The solution was then evacuated and 100 ml of methanol added. 2,6-diacetylpyridinebis(2,4,6-trimethylphenyl amine) precipitated out and was isolated by filtration and washed with 3 aliquots of 10 ml of methanol.

3.19 g of iron(II) chloride were weighed into a half litre Schlenk tube and 400 ml of n-butanol added. The suspension was warmed to 90° C. and stirred for 3 hours. 10 g of 2,6-diacetylpyridinebis(2,4,6-trimethylphenyl amine) was added as a solid at 80° C. The reaction was stirred for 1 hour then at 25° C. over 3 days. The resultant blue suspension was allowed to settle and the supernatant liquid decanted off. 2 washes of the precipitate with 200 ml aliquots of toluene were carried out, followed by one wash with 100 ml of n-pentane. The residual blue solid was pumped in vacuo for 6 hours till dry. It was stored and handled in a nitrogen atmosphere.

TITANIUM

Example 2

Preparation of the Catalyst

The equipment used for calcining the silica support was composed essentially of a vertical quartz cylinder, 75 cm high and 5 cm in diameter, above which was placed a disengagement zone. This calcinator was equipped with a fluidisation grid made from porous quartz and positioned in the lower part of the quartz cylinder. It was also equipped with an electrical resistance heater and a supply of fluidising nitrogen.

Into the calcinator maintained at 60° C. and supplied with nitrogen containing less than 2 vpm of water vapour and with a flow rate of 6.7 ml/s, were charged 20 g of silica sold under the trade name of ES70X by Crosfield Catalysts (Warrington, England). Next the calcinator was heated from 60 to 150° C. at a rate of 100° C./h. The silica was then maintained at 150° C. for 1 hour and 30 minutes in the fluidised state. Thereafter 14.8 g of a mixture of titanium tetraisopropoxide and tetra-n-butylate sold under the registered trade mark "Tilcom BIP" by Titanium Intermediates, Billingham, England was added dropwise to the fluidising silica. The treated silica was then maintained at 150° C. for 1 hour in the fluidised state. Next the calcinator and its contents were heated from 150 to 600° C. at a rate of 100° C./h. The calcinator and its contents were then maintained at 600° C. for 5 hours in the fluidised state. The calcinator and its contents were then cooled to room temperature at a rate of 100° C./h and the support was recovered and stored under dry nitrogen.

All subsequent operations were carried out in a nitrogen atmosphere. 3.946 g of the titanium treated silica thus dried were suspended in a solution of 0.34 g of methylaluminoxane (Witco, Bergkamen, Germany) in 17.1 g of toluene. The suspension was agitated for 2 hours at 25° C. The silica thus treated was washed five times with 20 ml of toluene. The treated silica was then dried under vacuum.

The treated silica was then suspended in 20 ml of toluene and 0.0698 g of the above iron complex (see Example 1) was added. The suspension was agitated for 17 hours at 25° C. The catalyst thus prepared was washed five times with 20 ml of toluene. The catalyst was then dried under vacuum.

The catalyst thus prepared contained 0.19% by weight of iron 2.0% by weight of titanium and 4.65% by weight of aluminium.

Example 3

Ethylene Polymerisation in the Gas Phase 400 g of polyethylene pellets were introduced into a stainless steel reactor of capacity 2.5 litres equipped with a stirrer and maintained under a nitrogen atmosphere. The reactor was heated to 97.1° C., stirred at 50 rpm and 0.7 g of silica previously treated with 1.5 mmole/g of triethylaluminium was added as poison scavenger. Next 0.0785 g of the above catalyst (see Example 2) was added. Then hydrogen was introduced to pressure the reactor to 0.05 MPa. Finally ethylene was fed until a total pressure of 0.8 MPa was obtained. Ethylene was fed to maintain this pressure throughout the reaction. After production corresponding to 50 g polyethylene per gram of catalyst, the stirring rate was increased to 100 rpm, after the production of 50 g of polyethylene the stirring rate was increased further to 150 rpm and after the production of 100 g of polyethylene the stirring rate was increased further to 200 rpm.

Polymerisation was allowed to continue for 4 hours and 13 minutes, during which period 150 g of polyethylene were produced. This corresponds to a catalyst yield of 1911 g polymer/g catalyst. The average activity during this polymerisation was 1766 g/mM.h.b. The reactor contents were cooled to 25° C. and were then recovered from the reactor. A sieve with 2 mm diameter mesh was used to separate the polyethylene pellets from the powder formed during the reaction. The recovered polymer powder had the following properties:

melt index (2.16 kg load) (MI)=0.53
melt index (21.6 kg load) (HLMI)=30.94
melt index ratio(HLMI/MI)=58.4
residual iron level=1.0 ppm Example 4 (Comparative)

Preparation of the Iron Complex as Catalyst Precursor

The iron complex prepared in Example 1 was employed.

Example 5 (Comparative)

Preparation of the Catalyst

Into the calcinator used in Example 2, maintained at 60° C. and supplied with nitrogen containing less than 2 vpm of water vapour and with a flow rate of 4.7 ml/s, were charged 30 g of silica sold under the trade name of ES70X by Crosfield Catalysts (Warrington, England). Next the calcinator was heated from 60 to 600° C. at a rate of 100° C./h.

The silica was then maintained at 600° C. for 16 hours in the fluidised state. The silica was then cooled to 25° C. and stored under dry nitrogen.

All subsequent operations were carried out in a nitrogen atmosphere. 12.5 g of the silica thus dried were suspended in a solution of 0.67 g of methylaluminoxane (Witco, Bergkamen, Germany) in 11.1 g of toluene. The suspension was agitated for 2 hours at 25° C. The silica thus treated was washed five times with 20 ml of toluene. The treated silica was then dried under vacuum. 2.87 g of the treated silica were suspended in 20 ml of toluene and 0.088 g of the above iron complex (see Example 1) was added. The suspension was agitated for 17 hours at 25° C. The catalyst thus prepared was washed five times with 20 ml of toluene. The catalyst was then dried under vacuum.

The catalyst thus prepared contained 0.47% by weight of iron and 2.88% by weight of aluminium.

Example 6 (Comparative)

Ethylene Polymerisation in the Gas Phase 400 g of polyethylene pellets were introduced into a stainless steel reactor of capacity 2.5 litres equipped with a stirrer and maintained under a nitrogen atmosphere. The reactor was heated to 97.9° C., stirred at 25 rpm and 0.7 g of silica previously treated with 1.5 mmole/g of triethylaluminium was added as poison scavenger. Next 0.1285 g of the above catalyst (see Example 5) was added. Then hydrogen was introduced to pressure the reactor to 0.06 MPa. Finally ethylene was fed until a total pressure of 0.8 MPa was obtained. Ethylene was fed to maintain this pressure throughout the reaction. After production corresponding to 50 g polyethylene per gram of catalyst, the stirring rate was increased to 100 rpm, after the production of 50 g of polyethylene the stirring rate was increased further to 150 rpm and after the production of 100 g of polyethylene the stirring rate was increased further to 200 rpm.

Polymerisation was allowed to continue for 4 hours and 57 minutes, during which period 263 g of polyethylene were produced. This corresponds to a catalyst yield of 2047 g polymer/g catalyst. The average activity during this polymerisation was 664 g/mM.h.b, compared with the 1766 g/mM.h.b in Example 1c of the invention. The reactor contents were cooled to 25° C. and were then recovered from the reactor. A sieve with 2 mm diameter mesh was used to separate the polyethylene pellets from the powder formed during the reaction. The recovered polymer powder had the following properties:

melt index (2.16 kg load) (MI)=0.45
melt index (21.6 kg load) (HLMI)=27.52
melt index ratio(HLMI/MI)=61.2
residual iron level=2.3 ppm

ALUMINIUM

Example 7

Preparation of the Catalyst

The equipment used for calcining the silica support was composed essentially of a vertical quartz cylinder, 75 cm high and 5 cm in diameter, above which was placed a disengagement zone. This calcinator was equipped with a fluidisation grid made from porous quartz and positioned in the lower part of the quartz cylinder. It was also equipped with an electrical resistance heater and a supply of fluidising nitrogen. Into the calcinator maintained at 60° C. and supplied with nitrogen containing less than 2 vpm of water vapour and with a flow rate of 6.7 ml/s, were charged 30 g of silica sold under the trade name of ES70X by Crosfield Catalysts (Warrington, England). Next the calcinator was heated from 60 to 200° C. at a rate of 100° C./h. The silica was then maintained at 200° C. for 5 hours in the fluidised state, and then cooled to 100° C. at a rate of 100° C./h, and 30 ml of a molar solution of triethylaluminium (Witco, Bergaman, Germany) added dropwise. The aluminium treated silica was then maintained at 100° C. for 1 hour in the fluidised state. Next the calcinator and its contents were heated from 100 to 600° C. at a rate of 100° C./h. The fluidising gas was changed from dry nitrogen to dry air. The calcinator and its contents were then maintained at 600° C. for 5 hours in the fluidised state. The fluidising gas was changed from dry air to dry nitrogen. The calcinator and its contents were then cooled to room temperature at a rate of 100° C./h and the support was recovered and stored under dry nitrogen.

All subsequent operations were carried out in a nitrogen atmosphere. 5.27 g of the aluminium treated silica thus dried were suspended in a solution of 0.33 g of methylaluminoxane (Witco, Bergkamen, Germany) in 17.1 g of toluene. The suspension was agitated for 2 hours at 25° C. The silica thus treated was washed five times with 20 ml of toluene. The treated silica was then dried under vacuum. 1.46 g of the treated silica was then suspended in 20 ml of toluene and 0.077 g of the above iron complex (see Example 1) was added. The suspension was agitated for 17 hours at 25° C. The catalyst thus prepared was washed five times with 20 ml of toluene. The catalyst was then dried under vacuum.

The catalyst thus prepared contained 0.47% by weight of iron and 6.0% by weight of aluminium.

Example 8

Ethylene Polymerisation in the Gas Phase 400 g of polyethylene pellets were introduced into a stainless steel reactor of capacity 2.5 litres equipped with a stirrer and maintained under a nitrogen atmosphere. The reactor was heated to 96.7° C., stirred at 50 rpm and 0.7 g of silica previously treated with 1.5 mmole/g of triethylaluminium was added as poison scavenger. Next 0.0635 g of the above catalyst (see Example 7) was added. Then hydrogen was introduced to pressure the reactor to 0.05 MPa. Finally ethylene was fed until a total pressure of 0.8 MPa was obtained. Ethylene was fed to maintain this pressure throughout the reaction. After production corresponding to 50 g polyethylene per gram of catalyst, the stirring rate was increased to 100 rpm, after the production of 50 g of polyethylene the stirring rate was increased further to 150 rpm and after the production of 100 g of polyethylene the stirring rate was increased further to 200 rpm.

Polymerisation was allowed to continue for 5 hours and 30 minutes, during which period 123 g of polyethylene were produced. This corresponds to a catalyst yield of 1937 g polymer/g catalyst. The reactor contents were cooled to 25° C. and were then recovered from the reactor. A sieve with 2 mm diameter mesh was used to separate the polyethylene pellets from the powder formed during the reaction. The recovered polymer powder had the following properties:

melt index (2.16 kg load) (MI)=0.21
melt index (21.6 kg load) (BLMI)=25.52
melt index ratio(HLMI/MI)=121.5
residual iron level=2.4 ppm Example 9 (Comparative)

Preparation of the Iron Complex as Catalyst Precursor

The iron complex prepared in Example 1 was employed.

Example 10

Preparation of the Catalyst

Into the calcinator used in Example 7, maintained at 60° C. and supplied with nitrogen containing less than 2 vpm of water vapour and with a flow rate of 4.7 ml/s, were charged 30 g of silica sold under the trade name of ES70X by Crosfield Catalysts (Warrington, England). Next the calcinator was heated from 60 to 600° C. at a rate of 100° C./h. The silica was then maintained at 600° C. for 16 hours in the fluidised state. The silica was then cooled to 25° C. and stored under dry nitrogen.

All subsequent operations were carried out in a nitrogen atmosphere. 12.5 g of the silica thus dried were suspended in a solution of 0.67 g of methylaluminoxane (Witco, Bergkamen, Germany) in 11.1 g of toluene. The suspension was agitated for 2 hours at 25° C. The silica thus treated was washed five times with 20 ml of toluene. The treated silica was then dried under vacuum. 2.87 g of the treated silica were suspended in 20 ml of toluene and 0.088 g of the above iron complex (see Example 1) was added. The suspension was agitated for 17 hours at 25° C. The catalyst thus prepared was washed five times with 20 ml of toluene. The catalyst was then dried under vacuum. The catalyst thus prepared contained 0.47% by weight of iron and 2.88% by weight of aluminium.

Example 11

Ethylene Polymerisation in the Gas Phase 400 g of polyethylene pellets were introduced into a stainless steel reactor of capacity 2.5 litres equipped with a stirrer and maintained under a nitrogen atmosphere. The reactor was heated to 94.8° C., stirred at 25 rpm and 0.7 g of silica previously treated with 1.5 mmole/g of triethylaluminium was added as poison scavenger. Next 0.1107 g of the above catalyst (see Example 7) was added. Then hydrogen was introduced to pressure the reactor to 0.04 MPa. Finally ethylene was fed until a total pressure of 0.8 MPa was obtained. Ethylene was fed to maintain this pressure throughout the reaction. After production corresponding to 50 g polyethylene per gram of catalyst, the stirring rate was increased to 100 rpm, after the production of 50, of polyethylene the stirring rate was increased further to 150 rpm and after the production of 100 g of polyethylene the stirring rate was increased further to 200 rpm.

Polymerisation was allowed to continue for 4 hours and 47 minutes, during which period 235 g of polyethylene were produced. This corresponds to a catalyst yield of 2123 g polymer/g catalyst. The reactor contents were cooled to 25° C. and were then recovered from the reactor. A sieve with 2 mm diameter mesh was used to separate the polyethylene pellets from the powder formed during the reaction. The recovered polymer powder had the following properties:

melt index (2.16 kg load) (MI)=0.26
melt index (21.6 kg load) (HLMI)=16.52
melt index ratio(HLMI/M)=63.5
residual iron level=2.2 ppm

I claim:

1. Catalyst for the polymerisation and copolymerisation of 1-olefins, comprising
   (1) a late transition metal complex
   (2) optionally an activating quantity of an activator compound, and
   (3) a support comprising silica, alumina, zirconia, talc, kieselguhr or magnesia, which has been impregnated with a titanium or aluminium compound, and calcined at a temperature of between 200° C. and 1000° C., said calcining being after impregnation in the case of aluminium.

2. Process for the preparation of a supported catalyst, comprising:
   preparing a support comprising silica, alumina, zirconia, talc, kieselguhr or magnesia, impregnating the support with a titanium or aluminium compound, then calcining the resulting titanium- or aluminium-impregnated support at a temperature of between 200 and 1000° C.;
   and then adding to the support a late transition metal complex and optionally an activating quantity of an activator compound.

3. Catalyst according to claim 1 wherein the titanium compound incorporated into the support is selected from compounds represented by the formulae (a) $(R')_n Ti(OR')_m$; (b) $(RO)_m Ti(OR')_n$; (c) $TiX_4$; (d) $TiO_2$; (e) titanium acetylacetonate compounds and (f) alkanolamine titanates; wherein m is 1, 2, 3 or 4; n is 0, 1, 2 or 3; m+n=4; the R group is selected from the group consisting of alkyl, aryl, cycloalkyl, arylalkyl and alkaryl, each group R having 1 to 12 carbon atoms; R' is selected from the group consisting of R, cyclopentadienyl and alkenyl, each group $R^1$ having 1 to 12 carbon atoms; X is halogen; and when more than one R or R' group occurs in the titanium compound the groups are the same or different.

4. Catalyst according to claim 1 wherein the titanium compound is a titanium acetylacetonate compound.

5. Catalyst according to claim 1 wherein the titanium compound is titanium triacetylacetonate, titanium dichlorodiacetylacetonate, titanium dichlorodi (isopropoxide), titanium tetramethoxide, titanium tetraethoxide, titanium tetraisopropoxide or titanium tetrabutoxide.

6. Catalyst according to claim 1 wherein the amount of titanium incorporated in the support is from 0.1 to 5 wt %.

7. Catalyst according to claim 1 wherein the aluminium compound incorporated into the support is selected from compounds represented by the formulae (a) $(R')_n Al(OR')_m$; (b) $(RO)_m Al(OR')_n$; (c) $(R')_n Al(X)_m$; (d) $Al_2O_3$; (e) aluminium acetylacetonate compounds and (f) alkanolamine aluminates wherein m is 0, 1, 2 or 3; n is 0, 1, 2 or 3; m+n=3; the R group is selected from the group consisting of alkyl, aryl, cycloalkyl, arylalkyl and alkaryl, each group R having 1 to 12 carbon atoms; R' is selected from the group consisting of R, cyclopentadienyl and alkenyl, each group R' having 1 to 12 carbon atoms; X is halogen; and when more than one R or R' group occurs in the aluminium compound the groups are the same or different.

8. Catalyst according to claim 1 wherein the aluminium compound is an aluminium acetylacetonate compound.

9. Catalyst according to claim 1 wherein the aluminium compound is aluminium acetylacetonate diisopropoxide, aluminium dichloro acetylacetonate, triethanolamine aluminate, trimethyl aluminium, triethyl aluminium or triisobutyl aluminium.

10. Catalyst according to claim 1 wherein the support is silica and the amount of aluminium impregnated in the silica is from 0.1 to 10 wt %.

11. Catalyst according to claim 1 wherein the calcining temperature is between 300 and 850° C.

12. Catalyst according to claim 1 wherein the support is additionally calcined at a temperature of between 250° C. and the sintering temperature of the support before the titanium or aluminium compound is impregnated into the support.

13. Catalyst according to claim 6, wherein the amount of titanium incorporated in the support is from 3 to 4.5 wt %.

14. Catalyst according to claim 1 wherein the late transition metal complex comprises a complex of the formula (I)

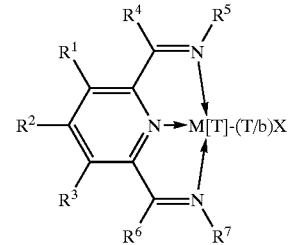

Formula (I)

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^7$ are each independently selected from the group consisting of hydrogen, halogen, hydrocarbyl, substituted hydrocarbyl, heterohydrocarbyl, substituted heterohydrocarbyl and $SiR'_3$ where each R' is independently selected from the group consisting of hydrogen, halogen, hydrocarbyl, substituted hydrocarbyl, heterohydrocarbyl, and substituted heterohydrocarbyl.

15. Catalyst according to claim 14 wherein $R^5$ is represented by the group "P" and $R^7$ is represented by the group "Q" as follows:

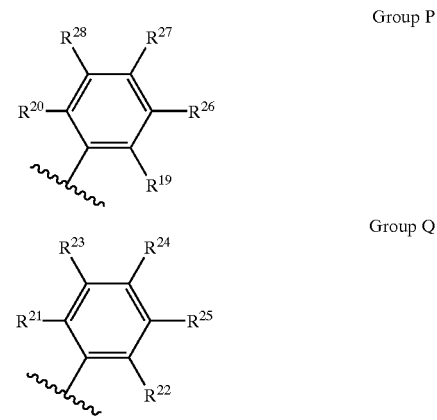

wherein $R^{19}$ to $R^{28}$ are independently selected from the group consisting of hydrogen, halogen, hydrocarbyl, substituted hydrocarbyl, heterohydrocarbyl and substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents.

16. Catalyst according to claim 14 wherein $R^5$ is represented by the group "P" and $R^7$ is represented by the group "Q" as follows:

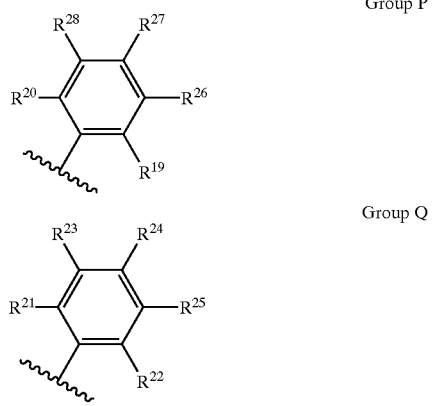

wherein $R^{23}$ to $R^{28}$ are independently selected from the group consisting of hydrogen, halogen, hydrocarbyl, substituted hydrocarbyl, heterohydrocarbyl and substituted heterohydrocarbyl, and $R^{19}$, $R^{20}$, $R^{21}$ and $R^{22}$ are each independently selected from the group consisting of methyl, ethyl, n-propyl, iso-propyl, n-butyl, sec-butyl, tert.-butyl, n-pentyl, neopentyl, n-hexyl, 4-methylpentyl, n-octyl, phenyl and benzyl.

17. Catalyst according to claim 14 wherein the complex of Formula (I) is selected from the group consisting of
2,6-diacetylpyridinebis(2,6-diisopropylanii)FeCl$_2$
2,6-diacetylpyridinebis(2,6-diisopropylanil)MnCl$_2$
2,6-diacetylpyridinebis(2,6-diisopropylanil)CoCl$_2$
2,6-diacetylpyridinebis(2-tert.-butylanil)FeCl$_2$
2,6-diacetyipyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl2
2,6-diacetylpyridinebis(2,4,6 trimethyl anil)FeCl$_2$
2,6,diacetylpyridinebis(2,6-dimethyl 4-t-butyl anil)FeCl$_2$
2,6-dialdiminepyridinebis(2,6-dimethylanil)FeCl2
2,6-dialdiminepyridinebis(2,6-diethylanil)FeCl$_2$
2,6-dialdiminepyridinebis(2,6-diisopropylanil)FeCl$_2$
2,6-dialdiminepyridinebis(1-naphthil)FeCl$_2$ and
2,6-bis(1,1-diphenylhydrazone)pyridine FeCl$_2$.

18. Catalyst according to claim 14 wherein the activator compound (2) is selected from the group consisting of organoaluminium compounds and hydrocarbylboron compounds.

19. Catalyst according to claim 14 wherein the activator compound (2) is selected from the group consisting of trimethylaluminium, triethylaluminium, tri-isobutylaluminium, tri-n-octyialuminium, methylaluminium dichloride, ethyfaluminium dichloride, dimethylaluminium chloride, diethylaluminium chloride, ethylaluminiumsesquichloride, methylaluminiumsesquichloride and an alumoxane.

20. Catalyst according to claim 19 wherein the alumoxane is methylalumoxane.

21. Catalyst according to claim 10 wherein the amount of aluminium impregnated in the silica is from 1 to 6 wt %.

22. Catalyst according to claim 21 wherein the amount of aluminium impregnated in the silica is from 1.5 to 2.5 wt %.

23. Catalyst according to claim 11 wherein the calcining temperature is between 400 and 750° C.

24. Process according to claim 2 wherein the amount of titanium incorporated in the support is from 0.1 to 5 wt %.

25. Process according to claim 24 wherein the amount of titanium incorporated in the support is from 3 to 4.5 wt %.

26. Process according to claim 2 wherein the aluminium compound is aluminium acetylacetonate dilsopropoxide, aluminium dichloro acetylacetonate, triethanolamine aluminate, trimethyl aluminium, triethyl aluminium or tri-isobutyl aluminium.

27. Process according to claim 2 wherein the aluminium compound is an aluminium acetylacetonate compound.

28. Process according to claim 2 wherein thetitanium compound incorporated into the support is selected from compounds represented by the formulae (a) $(R')_n Ti(OR')_m$; (b) $(RO)_m Ti(OR')_n$; (c) $TiX_4$; (d) $TiO_2$; (e) titanium acetylacetonate compounds and (f) alkanolamine titanates; wherein m is 1, 2, 3 or 4; n is 0, 1, 2 or 3; m+n=4; the R group is selected from the group consisting of alkyl, aryl, cycloalkyl, arylalkyl and alkaryl, each group R having 1 to 12 carbon atoms; R' is selected from the group consisting of R, cyclopentadienyl and alkenyl, each group R' having 1 to 12 carbon atoms; X is halogen; and when more than one R or R' group occurs in the titanium compound the groups are the same or different.

29. Process according to claim 2 wherein the titanium compound is a titanium acetylacetonate compound.

30. Process according to claim 2 wherein the titanium compound is titanium triacetylacetonate, titanium dichlorodiacetylacetonate, titanium dichlorodi (isopropoxide), titanium tetramethoxide, titanium tetraethoxide, titanium tetraisopropoxide or titanium tetrabutoxide.

31. Process according to claim 2 wherein the calcining temperature is between 300 and 850° C.

32. Process according to claim 31 wherein the calcining temperature is between 400 and 750° C.

33. Process according to claim 2 wherein the aluminium compound incorporated into the support is selected from compounds represented by the formulae (a) $(R')_n Al(OR')_m$; (b) $(RO)_m Al(OR')_n$; (c) $(R')_n Al(X)_m$; (d) $Al_2O_3$; (e) aluminium acetylacetonate compounds and (f) alkanolamine aluminates wherein m is 0, 1, 2 or 3; n is 0, 1, 2 or 3; m+n=3; R group is selected from the group consisting of alkyl, aryl, cycloalkyl, arylalkyl and alkaryl, each group R having 1 to 12 carbon atoms; R' is selected from the group consisting of R, cyclopentadienyl and alkenyl, each group R' having 1 to 12 carbon atoms; X is halogen; and when more than one R or R' group occurs in the aluminium compound the groups are the same or different.

34. Process according to claim 2 wherein the late transition metal complex comprises a complex of the formula (I)

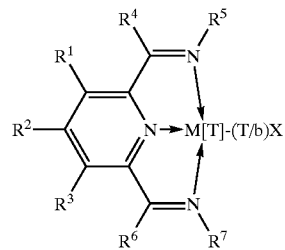

Formula (I)
wherein M is Fe[II], Fe[III], Co[I], Co[II], Co[III], Mn[I], Mn[II], Mn[III], Mn[IV], Ru[II], Ru[III] or RU[IV]; X represents an atom or group covalently or ionically bonded to the transition metal M; T is the oxidation state of the transition metal M and b is the valency of the atom or group X; $R^1$ to $R^7$ fare each independently selected from the group consisting of hydrogen, halogen, hydrocarbyl, substituted hydrocarbyl, heterohydrocarbyl, substituted heterohydrocarbyl and $SiR'_3$ where each R' is independently selected from the group consisting of hydrogen, halogen, hydrocarbyl, substituted hydrocarbyl, heterohydrocarbyl, and s ero-hydrocarbyl.

35. Process according to claim 34 wherein $R^5$ is represented by the group "P" and $R^7$ is represented by the group "Q" as follows:

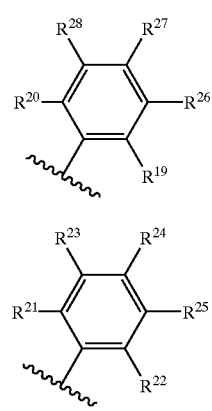

Group P

Group Q wherein $R^{19}$ to $R^{28}$ are independently selected from the group consisting of hydrogen, halogen, hydrocarbyl, substituted hydrocarbyl, heterohydrocarbyl and substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents.

36. Process according to claim 2 wherein the support is silica and the amount of aluminium impregnated in the silica is from 0.1 to 10 wt %.

37. Process according to claim 36 wherein the amount of aluminium impregnated in the silica is from 1 to 6 wt %.

38. Process according to claim 37 wherein the amount of aluminium impregnated in the silica is from 1.5 to 2.5 wt %.

39. Process according to claim 2 wherein the support is additionally calcined at a temperature of between 250° C. and the sintering temperature of the support before the titanium or aluminium compound is impregnated into the support.

40. Process according to claim 34 wherein the activator compound (2) is selected from the group consisting of trimethyfaluminium, triethylaluminium, tri-isobutylaluminium, tri-n-octylaluminium, methylaluminium dichloride, ethylaluminium dichloride, dimethylaluminium chloride, diethylaluminium chloride, ethylaluminiumsesquichloride, methylaluminiumsesquichloride and an alumoxane.

41. Process according to claim 40 wherein the alumoxane is methylalumoxane.

42. Process according to claim 34 wherein the activator compound (2) is selected from the group consisting of organoaluminium compounds and hydrocarbylboron compounds.

43. Process according to claim 34 wherein the complex of Formula (I) is selected from the group consisting of 2,6-diacetylpyridinebis(2,6-diisopropylanil)$FeCl_2$
2,6-diacetylpyridinebis(2,6-diisopropylanil)$MnCl_2$
2,6-diacetylpyridinebis(2,6-diisopropylanil)$CoCl_2$
2,6-diacetylpyridinebis(2-tert.-butylanil)$FeCl(_2$
2,6-diacetylpyridinebis(2,3-dimethylanil)$FeCl_2$
2,6-diacetylpyridinebis(2-methylanil)$FeCl_2$
2,6-diacetylpyridinebis(2,4-dimethylanil)$FeCl_2$
2,6-diacetylpyridinebis(2,6-dimethylanil)$FeCl_2$
2,6-diacetylpyridinebis(2,4,6 trimethyl anil)$FeCl_2$
2,6-diacetylpyridinebis(2,6-dimethyl 4-t-butyl anil)$FeCl_2$
2,6-dialdiminepyridinebis(2,6-dimethylanil)$FeCl_2$
2,6-dialdiminepyridinebis(2,6-diethylanil)$FeCl_2$
2,6-dialdiminepyridinebis(2,6-diisopropylanil)$FeCl_2$
2,6-dialdiminepyridinebis(1-naphthil)$FeCl_2$ and
2,6-bis(1,1-diphenylhydrazone)pyridine $FeCl_2$.

44. Process according to claim 34 wherein $R^5$ is represented by the group "P" and $R^7$ is represented by the group "Q" as follows:

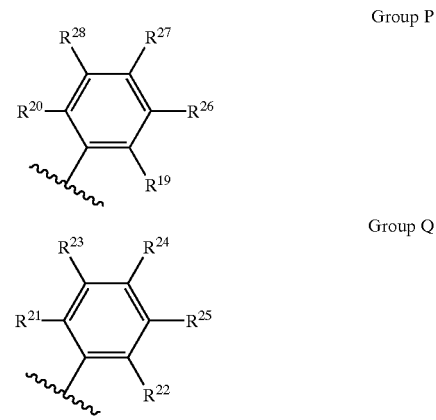

Group P

Group Q wherein $R^{23}$ to $R^{28}$ are independently selected from the group consisting of hydrogen, halogen, hydrocarbyl, substituted hydrocarbyl, heterohydrocarbyl and substituted heterohydrocarbyl, and $R^{19}$, $R^{20}$, $R^{21}$ and $R^{22}$ are each independently selected from the group consisting of methyl, ethyl, n-propyl, iso-propyl, n-butyl, sec-butyl, tert.-butyl, n-pentyl, neopentyl, n-hexyl, 4-methyipentyl, n-octyl, phenyl and benzyl.

* * * * *

UNITED STATES PATENT AND TRADEMARK OFFICE
CERTIFICATE OF CORRECTION

PATENT NO. : 6,492,293 B1
DATED : December 10, 2002
INVENTOR(S) : John Gabriel Speakman It is certified that error appears in the above-identified patent and that said Letters Patent is hereby corrected as shown below:

Column 17,
Line 31, "$R^1$" should read -- R' --.

Column 18,
Line 40, "$R^7$is" should read -- $R^7$ is --.

Column 19,
Line 32, "2,6-diacetylpyridinebis(2,6-diisopropylanii)$FeCl_2$" should read
-- 2,6-diacetylpyridinebis(2,6-diisopropylanil)$FeCl_2$ --.
Line 37, "2,6-diacetyipyridinebis(2,3-dimethylanil)$FeCl_2$" should read
-- 2,6-diacetylpyridinebis(2,3-dimethylanil)$FeCl_2$ --.
Line 41, "2,6-diacetylpyridinebis(2,6-dimethylanil)FeCl2" should read
-- 2,6-diacetylpyridinebis(2,6-dimethylanil)$FeCl_2$ --.
Line 43, "2,6,diacetylpyridinebis(2,6-dimethyl 4-t-butyl anil)$FeCl_2$" should read
-- 2,6-diacetylpyridinebis(2,6-dimethyl 4-t-butyl anil)$FeCl_2$ --.
Line 44, "2,6-dialdiminepyridinebis(2,6-dimethylanil)FeCl2" should read
-- 2,6-dialdiminepyridinebis(2,6-dimethylanil)$FeCl_2$ --.
Line 57, "tri-n-octyialuminium" should read -- tri-n-octylaluminium --.
Line 58, "ethyfaluminium" should read -- ethylaluminium --.

Column 20,
Line 8, "dilsopropoxide" should read -- diisopropoxide --.
Line 13, "thetitanium" should read -- the titanium --.
Line 67, "RU[IV];" should read -- Ru[IV]; --.

Column 21,
Line 1, "tonically" should read -- ionically --.
Line 4, "fare" should read -- are --.
Lines 10-11, "s erohydrocarbyl" should read -- substituted heterohydrocarbyl --.
Line 54, "trimethyfaluminium" should read -- trimethylaluminium --.

UNITED STATES PATENT AND TRADEMARK OFFICE
CERTIFICATE OF CORRECTION

PATENT NO. : 6,492,293 B1
DATED : December 10, 2002
INVENTOR(S) : John Gabriel Speakman It is certified that error appears in the above-identified patent and that said Letters Patent is hereby corrected as shown below:

Column 22,
Line 13, "2,6-diacetylpyridinebis(2-tert.-butylanil)FeCl($_2$" should read
-- 2,6-diacetylpyridinebis(2-tert.-butylanil)FeCl$_2$ --.
Line 57, "4-methyipentyl" should read -- 4-methylpentyl --.

Signed and Sealed this

Seventeenth Day of June, 2003

JAMES E. ROGAN
*Director of the United States Patent and Trademark Office*